US00PP30736P3

(12) United States Plant Patent
Bernardini

(10) Patent No.: US PP30,736 P3
(45) Date of Patent: Jul. 23, 2019

(54) STRAWBERRY PLANT NAMED 'SWTCOL'

(50) Latin Name: ***Fragaria* x *ananassa* Duchesne ex Rozier**
Varietal Denomination: SWTCOL

(71) Applicant: HARGREAVES PLANTS LTD, Norfolk (GB)

(72) Inventor: Danilo Bernardini, Cesena (IT)

(73) Assignee: HARGREAVES PLANTS LTD, Norfolk (GB)

( * ) Notice: Subject to any disclaimer, the term of this patent is extended or adjusted under 35 U.S.C. 154(b) by 0 days.

(21) Appl. No.: 15/732,131

(22) Filed: Sep. 21, 2017

(65) Prior Publication Data

US 2018/0124974 P1 May 3, 2018

(30) Foreign Application Priority Data

Oct. 31, 2016 (QZ) ..... PBR 20162646

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 5/08* (2013.01)

(58) Field of Classification Search
USPC ..... Plt./208, 209
CPC ..... A01H 5/08; A01H 5/0893; A01H 6/7409; A01H 5/0868
See application file for complete search history.

(56) References Cited

PUBLICATIONS

Community Plant Variety Office (CPVO) application No. 201603090 for NF 195B filed Oct. 31, 2016, p. 6. (Year: 2016).*
Aehageman Roys Plants and Flowers Strawberry Plants—Sweet Colossus 2016, retrieved on Aug. 23, 2018, retrieved from the Internet at http://roysplantsandflowers.com/index.php/2016/05/14/strawberry-plants-sweet-colossus/, one page. (Year: 2016).*
Pluto Plant Variety Database 20180822, retrieved on Aug. 23, 2018, retrieved from the Internet at https://www3.wipo.int/pluto/user/en/index.jsp, one page. (Year: 2018).*

* cited by examiner

*Primary Examiner* — June Hwu
(74) *Attorney, Agent, or Firm* — Jondle & Associates, P.C.

(57) ABSTRACT

A new and distinct variety of strawberry plant named 'SWTCOL' particularly characterized by having very large fruit with a conical shape and mid-season harvest maturity, is disclosed.

3 Drawing Sheets

Genus and species: *Fragaria* x *ananassa* Duchesne ex Rozier.

Variety denomination: 'SWTCOL'.

CROSS REFERENCE TO RELATED APPLICATIONS

This application claims the benefit of priority from EU Community Plant Variety Rights (CPVO) application no. 2016/2646, filed Oct. 31, 2016, which is incorporated herein by reference in its entirety.

BACKGROUND OF THE NEW PLANT

The present invention relates to a new and distinct strawberry variety designated 'SWTCOL' and botanically known as *Fragaria* x *ananassa*. This new strawberry variety was discovered as a seedling in Cesena, Italy and originated from a controlled cross made in July 2005 in Cesena, Italy between the female parent 'NF 101' (unpatented) and the male parent 'NF 302' (unpatented). A single plant was selected for asexual propagation via stolons/runners in Cesena, Italy.

The present invention has been found to retain its distinctive characteristics through successive asexual propagations via stolons.

Plant Breeder's Rights for this variety have been applied for in Europe on Oct. 31, 2016. 'SWTCOL' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Sutton Bridge, Lincolnshire, U.K.

1. Very large fruit;
2. Conical shape; and
3. Mid-season harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from 10-12 month-old plants.

Figure 1:
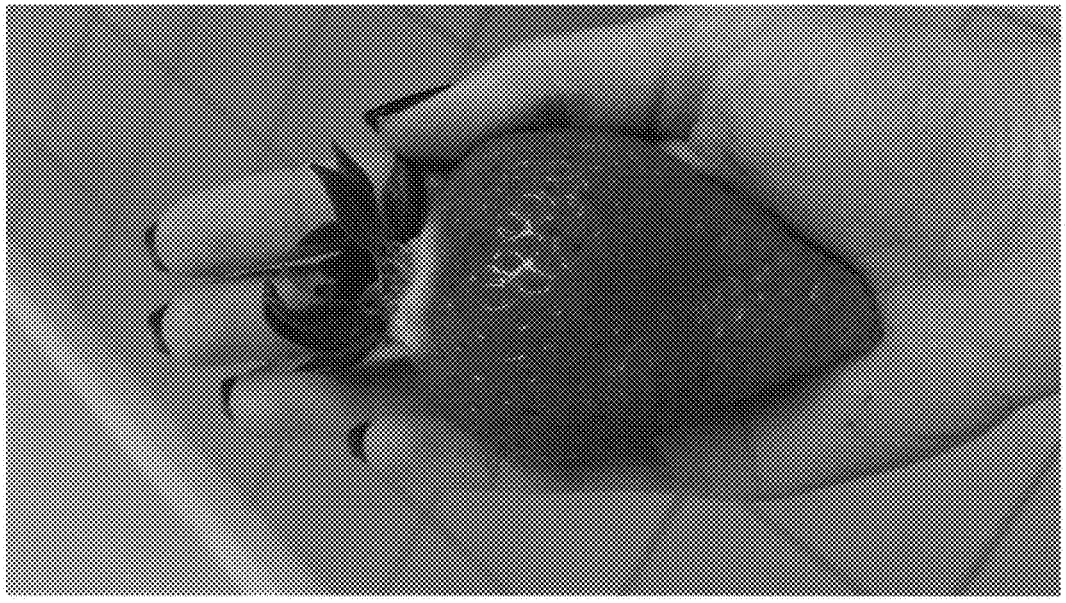
Figure 2:
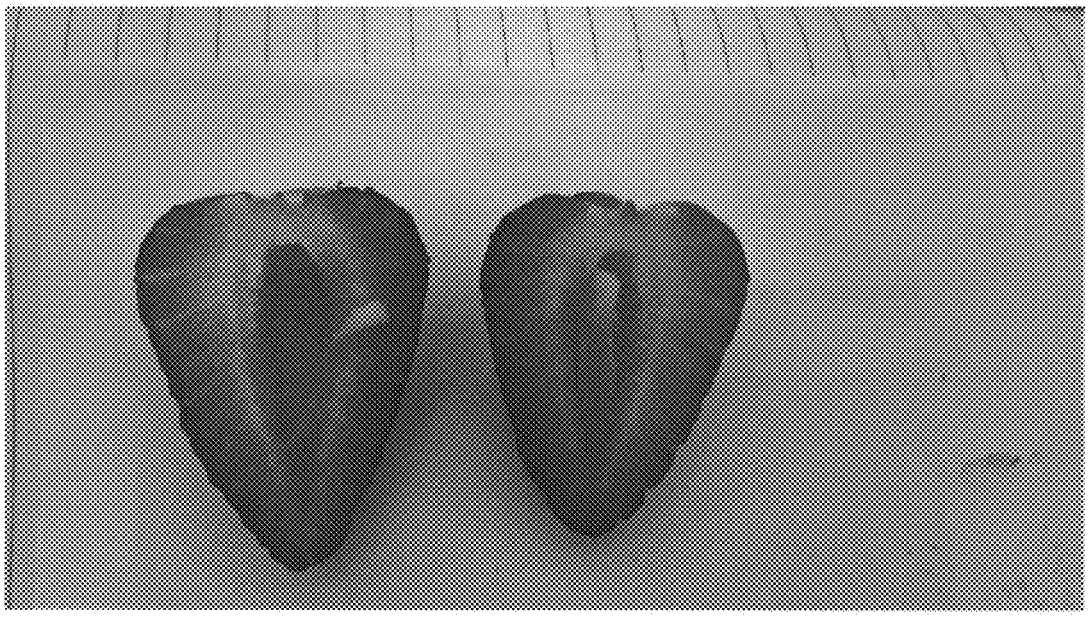
Figure 3:
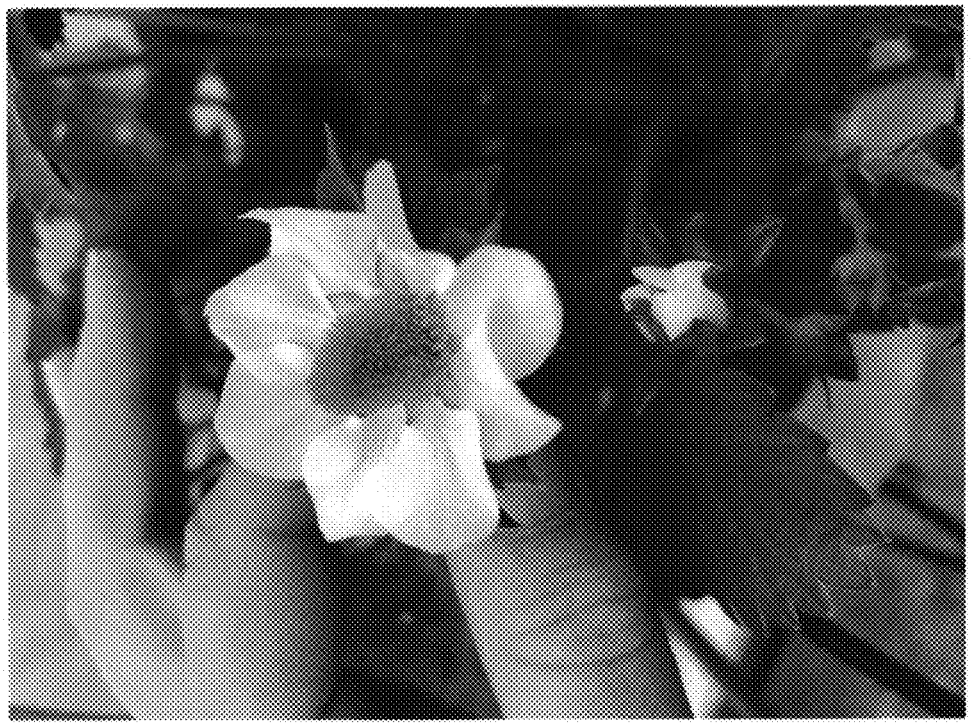

FIG. 1 shows a close-up of the whole fruit.
FIG. 2 shows the fruit in longitudinal cross-section.
FIG. 3 shows a close-up of a flower upper surface.

Figure 4:
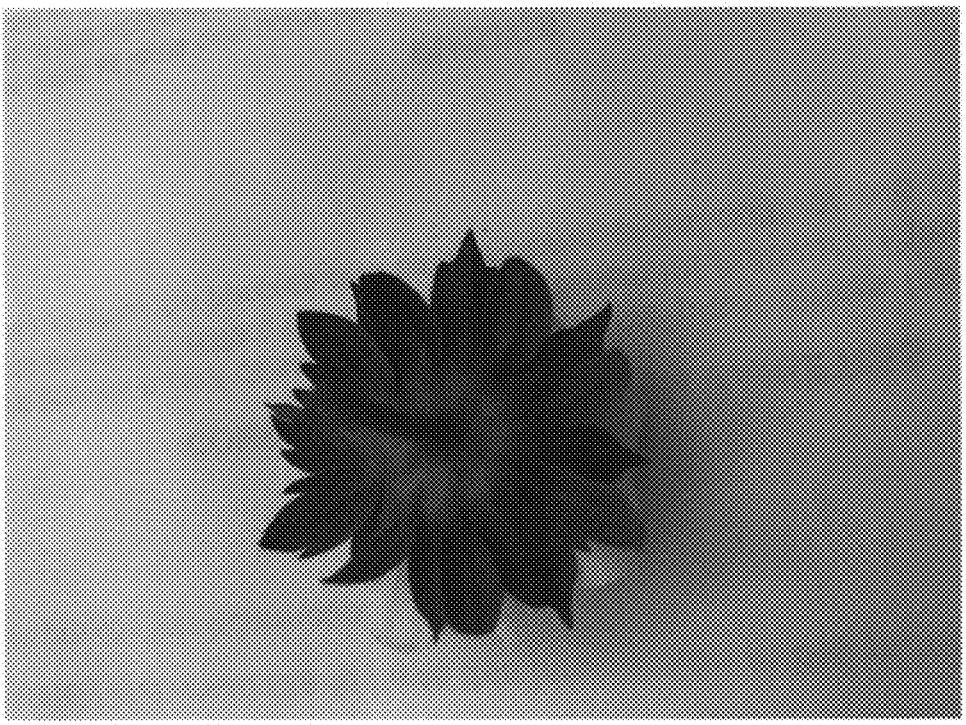
Figure 5:
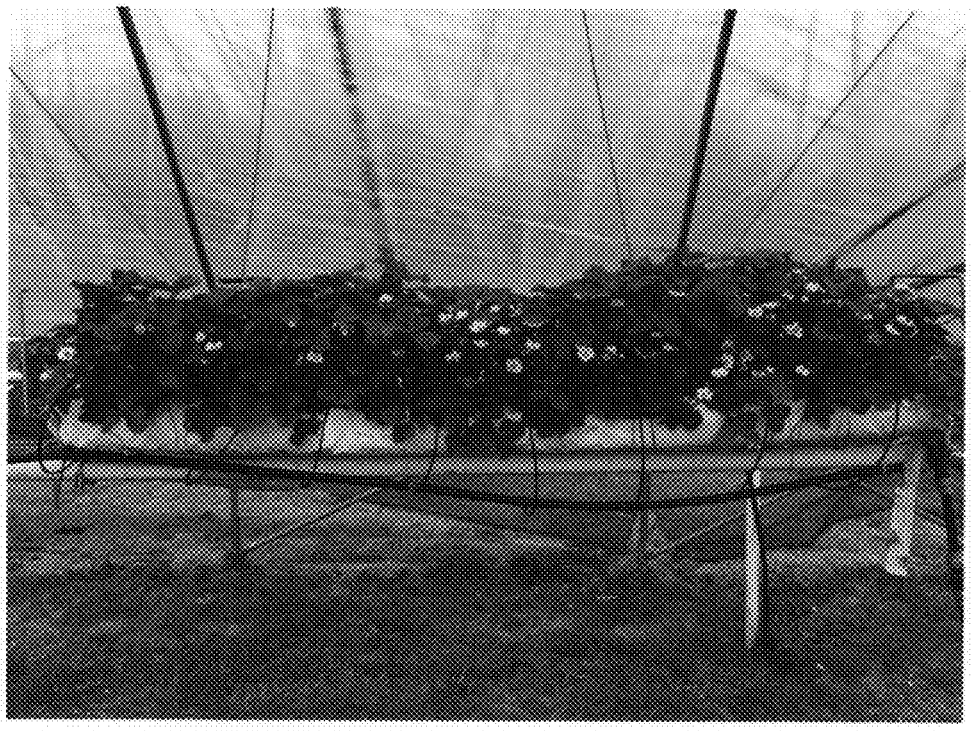
Figure 6:
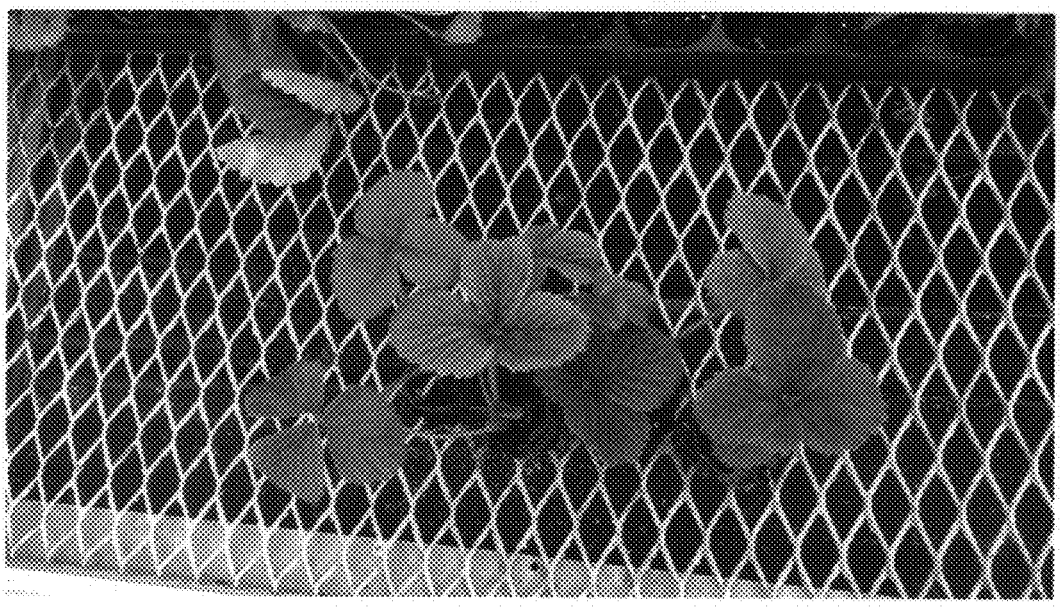

FIG. 4 shows a close-up of a flower lower surface.
FIG. 5 shows overall plant habit of numerous plants.
FIG. 6 shows a close-up of overall plant habit.

DESCRIPTION OF THE NEW VARIETY

The following detailed descriptions set forth the distinctive characteristics of 'SWTCOL'. The data which define these characteristics is based on observations taken in Sutton Bridge, Lincolnshire, U.K. This description is in accordance with UPOV terminology. Color designations, color descriptions, and other phenotypical descriptions may deviate from the stated values and descriptions depending upon variation in environmental, seasonal, climatic, and cultural conditions. 'SWTCOL' has not been observed under all possible environmental conditions. Color references are primarily to The R.H.S. Colour Chart of The Royal Horticultural Society of London 5$^{th}$ Edition. Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:
- *Family*.—Rosaceae.
- *Species*.—*Fragaria* x *ananassa* Duchene ex Rozier.
- *Common name*.—Strawberry.
- *Denomination*.—'SWTCOL'.

Parentage:
- *Female parent*.—'NF 101' (unpatented).
- *Male parent*.—'NF 302' (unpatented).

Plant:
- *Growth habit*.—Upright.
- *Height*.—33.0 cm.
- *Diameter*.—22.0 cm.
- *Number of crowns/plant*.—5.
- *Vigor*.—Good.

Terminal leaflets:
- *Size*.—Length: 10.7 cm. Width: 8.0 cm. Length/width ratio: 1.3.
- *Number of teeth/terminal leaflet*.—25.
- *Shape of teeth*.—Rounded.
- *Color*.—Upper surface: RHS 138B. Lower surface: RHS 139B.
- *Shape in cross section*.—Concave.
- *Blistering*.—Medium.
- *Glossiness*.—Medium.
- *Number of leaflets*.—3.
- *Base shape*.—Obtuse.
- *Apex descriptor*.—Rounded.
- *Pubescence color*.—Upper surface: RHS 139B. Lower surface: RHS 145B.
- *Margin*.—Serrate to crenate.
- *Texture*.—Slightly waxy, medium to rough.
- *Venation pattern*.—Pinnate. Color: Upper surface: RHS 139B. Lower surface: RHS 145B.

Petiole:
- *Length*.—25.0 cm.
- *Diameter*.—0.37 cm.
- *Color*.—RHS 145B.
- *Pubescence density*.—Medium. Color: RHS 145B.
- *Anthocyanin*.—Absent.
- *Pose of hairs*.—Slightly outward.
- *Texture*.—Rough.

Petiolule:
- *Length*.—1.0 cm.
- *Diameter*.—0.185 cm.
- *Color*.—RHS 145B.

Stipule:
- *Length*.—1.4 cm.
- *Width*.—0.91 cm.
- *Texture* (*both upper and lower surfaces*).—Smooth.
- *Color*.—RHS 48A.
- *Anthocyanin*.—Present.

Stolon:
- *Number of daughter plants*.—54 tips per mother plant.
- *Anthocyanin*.—Absent.
- *Thickness*.—0.39 cm.
- *Pubescence*.—Moderate.

Inflorescence:
- *Position relative to foliage*.—Above.
- *Time of flowering* (50% *of plants at first flower*).—May 5, 2017.
- *Corolla*.—Form: Petals overlapping. Length: 3.14 cm. Width: 3.1 cm. Depth: 0.79 cm.
- *Petals*.—Number per flower: 7. Shape: Globose oblate. Apex: Truncate to obtuse. Base: Attenuate. Margin: Smooth. Spacing: Overlapping. Length: 1.5 cm. Width: 1.55 cm. Length/width ratio: 0.97. Color (upper surface): White (RHS 155D). Texture: Smooth.
- *Calyx*.—Diameter: 4.5 cm. Diameter of calyx relative to corolla on secondary flowers: Same size. Inner calyx diameter relative to outer on secondary flowers: Same size. Position of calyx attachment: Raised/upright.
- *Sepal*.—Margin: Smooth. Length: 1.2 cm. Width: 0.60 cm. Typical and observed sepal number per flower: 14. Color: RHS 137B with RHS N144B stripes up the center. Anthocyanin: Absent. Texture (both upper and lower surfaces): Smooth. Attitude of sepal on fruit: Upward.
- *Peduncle*.—Length: 39.4 mm. Diameter: 2.3 mm. Color: RHS 145B. Pubescence: Medium.

Reproductive organs:
- *Stamens*.—Number: 27. Color: RHS 150B. Filament: Length: 2.9 mm. Diameter: 0.4 mm. Anthers: Color: RHS 17B. Length: 1.39 mm. Diameter: 1.3 mm. Pollen amount: Medium. Color: RHS 17B.
- *Pistils*.—Style: Length (including stigma): 1.0 mm. Diameter (including stigma): 0.1 mm. Color: RHS 17B. Stigma: Color: RHS 17B.
- *Receptacle color*.—RHS 17B.

Fruiting truss:
- *Length*.—97.24 mm.
- *Attitude at first picking*.—Hanging down.

Fruit:
- *Size*.—Very large.
- *Length*.—6.0 cm.
- *Width*.—3.6 cm.
- *Length/width ratio*.—1.6.
- *Fruit hollow center* (*cavity*).—Small to medium.
- *Weight* (*per individual berry*).—30.0 g.
- *Predominant fruit shape*.—Conical.
- *Difference in shape between primary and secondary fruits*.—None.
- *Fruit skin color*.—Medium red (RHS 46B).
- *Evenness of fruit color*.—Very even.
- *Fruit glossiness*.—Medium.

*Attitude of calyx segments*.—Upright.

*Achenes*.—Insertion of achenes: Below the surface. Color: RHS 1A. Width of band without achenes: Very small.

*Firmness of flesh* (*when fully ripe*).—Medium to firm.

*Firmness of skin*.—Medium to firm.

*Internal color*.—The color starts at the edge of the cut fruit with a reddish color (RHS 44C) then turns slightly orange (RHS 29B).

*Color of core*.—RHS 35A.

*Sweetness*.—Very sweet.

*Acidity*.—Not measured.

*Type of bearing*.—Not remontant.

*Grams of fruit/plant*.—360.0 g.

*Time of ripening* (*50% of plants with first ripe fruit*).—Jun. 5, 2017.

*Shipping and storage quality*.—Good.

*Fruit market use*.—Commercial fruit market.

Disease and pest resistance: Not tested to date.

COMPARISON WITH PARENTAL AND SIMILAR COMMERCIAL VARIETIES

The female parent plant of 'SWTCOL', cultivar 'NF 101' (unpatented), is no longer in existence, so a meaningful comparison cannot be made.

The male parent plant of 'SWTCOL', cultivar 'NF 302' (unpatented), is no longer in existence, so a meaningful comparison cannot be made.

When 'SWTCOL' is compared to the commercial variety 'Maxim' (U.S. Plant Pat. No. 5,782), 'SWTCOL' has conical shaped fruit, whereas 'Maxim' has round fruit.

When 'SWTCOL' is compared to the commercial variety 'Alba' (unpatented), 'SWTCOL' has a mid-season harvest maturity, whereas 'Alba' has an early harvest maturity.

When 'SWTCOL' is compared to the commercial variety 'Sweetheart' (unpatented), 'SWTCOL' has very large fruit, whereas 'Sweetheart' has medium sized fruit.

I claim:

1. A new and distinct variety of strawberry plant named 'SWTCOL', substantially as described and illustrated herein.

* * * * *